United States Patent [19]
Srivastava et al.

[11] Patent Number: 6,130,087
[45] Date of Patent: Oct. 10, 2000

[54] METHODS FOR GENERATING CYTOTOXIC T CELLS IN VITRO

[75] Inventors: Pramod K. Srivastava, Riverdale; Robert Binder; Nathalie E. Blachere, both of Bronx, all of N.Y.

[73] Assignee: Fordham University, Bronx, N.Y.

[21] Appl. No.: 08/726,967

[22] Filed: Oct. 7, 1996

[51] Int. Cl.[7] ............................... C12N 5/06; C12N 5/08
[52] U.S. Cl. .................. 435/372.3; 435/375; 435/377
[58] Field of Search ............................ 435/372.3, 377, 435/375

[56] References Cited

U.S. PATENT DOCUMENTS 4,690,915  9/1987  Rosenberg .

FOREIGN PATENT DOCUMENTS

| 196 02 985 A1 | 7/1997 | Germany . |
|---|---|---|
| WO 89/12455 | 12/1989 | WIPO . |
| WO 94/29459 | 12/1994 | WIPO . |
| WO 97/06685 | 2/1997 | WIPO . |
| WO 97/06821 | 2/1997 | WIPO . |
| WO 97/06828 | 2/1997 | WIPO . |
| WO 97/26910 | 7/1997 | WIPO . |

OTHER PUBLICATIONS

Engers et al. S. of Immunology 115:356–360, 1975.
Umezu et al. Cancer Immunol. Immunother. 37:392–397. 1993.
Nair et al. J. of Imm. Methods 152:232. 1992.
Anichini et al., 1987, Immunol. Today 8:385–389.
Barrios, 1992, Eur. J. Immunol. 22:1365–1372.
Bartlett, 1972, J. Natl. Cancer Inst. 49:493–504.
Berke, 1995, Cell 81:9–12.
Bevan, 1995, J. Exp. Med. 182:639–641.
Blachere and Srivastava, 1993, J. Cell. Biochem. Keystone Symp. NZ502, p. 124.
Blachere er al., 1993, J. Immunother. 14:352–356.
Cohen, 1987, *Basic and Clinical Immunology* (Appleton & Lange, Norwalk) pp. 669–689.
Falk et al., 1990, Nature 348:248–251.
Falk et al., 1991, Nature 351:290–296.
Fathman et al., 1989, *Fundamental Immunology* (Raven Press Ltd., New York) pp. 803–815.
Feldweg and Srivastava, 1993, J. Cell. Biochem. Suppl., yAbstract NZ 108.
Fossati et al., 1982, Cancer Immunol. Immunother. 14:99–104.
Gartner et al., 1986, Science 233:215–217.
Greenberg et al., 1983, *Basic and Clinical Tumor Immunology* (Martinus Nijhoff Publishers, Boston) pp. 301–335.
Grimm et al., 1982, J. Exp. Med. 155:1823–1841.
Herin et al., 1987, Int. J. Cancer 39:390–396.
Hersey et al., 1981, Int. J. Cancer 28:695–703.
Lakey et al., 1997, Proc. Natl. Acad. Sci. USA 84:1659–1663.
Lanzavecchia, 1993, Curr. Opin. Immunol. 8:348–354.
Lanzavecchia, 1993, Science 260:937–944.
Levy, 1991, Cell 67:265–274.
Li and Srivastava, 1993, EMBO J. 12:3143–3151.
Lindquist and Craig, 1988, Ann. Rev. Genet. 22:631–677.
Luescher et al., 1991, Nature 351:72–77.
Lussow et al., 1991, Eur. J. Immunol. 21:2297–2302.
Melief and Kast, 1992, *Cancer Surveys Vol. 13: A New Look at Tumor Immunology*, Imperial Cancer Research Fund pp. 81–99.
Mule et al., 1984, Science 225:1487–1489.
Old et al., 1962, Ann. N.Y. Acad. Sci. 101:80–106.
Palladino et al., 1987, Cancer Res. 47:5074–5079.
Rosenberg et al., 1988, New Engl. J. Med. 316:889–897.
Rosenberg et al., 1988, New Engl. J. Med. 319:1676–1680.
Rotzschke et al., 1990, Nature 348:248–251.
Rudensky et al., 1991, Nature 353:622–627.
Sallusto and Lanzavecchia, 1994, J. Exp. Med. 179:1109–1118.
Schumacher et al., 1991, Nature 350:703–706.
Slovin et al., 1986, J. Immunol. 9:3042–3048.
Srivastava et al., 1994, Immunogenetics 39:93–98.
Srivastava et al., 1987, Proc. Natl. Acad. Sci. USA 84:3807–3811.
Srivastava and Maki, 1991, Microbiol. Immunol. 167:109–123.
Srivastava and Heike, 1986, Sem. in Immunol. 3:57–64.
Srivastava et al., 1989, Cancer Res. 49:1341–1343.
Srivastava et al., 1986, Proc. Natl Acad. Sci. USA 83:3407–3411.
Srivastava et al., 1991, Curr. Opin. Immunol. 3:654–658.
Srivastava et al., 1984, Int. J. Cancer 33:417–422.
Srivastava et al., 1988, Immunol. Today 9:78–83.
Suto and Srivastava, 1995, Science 269:1585–1588.
Taylor and Cohen, 1992, Curr. Opin. Immunol. 4:338–343.
Topallian et al., 1989, J. Immunol. 142:3714–3725.
Udono et al., 1993, J. Exp. Med. 178:1391–1396.
Udono, 1993, J. Cell. Biochem. Suppl. 17D:113 (Abs. NZ225).
Ullrich et al., 1986, Proc. Natl. Acad. Sci. USA 83:3121–3125.

(List continued on next page.)

*Primary Examiner*—Thomas M. Cunningham
*Assistant Examiner*—Martha T. Lubet
*Attorney, Agent, or Firm*—Pennie & Edmonds LLP

[57] ABSTRACT

The present invention provides methods for generating antigen-reactive cytotoxic T cells in vitro comprising culturing immune cells and antigenic cells that have at least one MHC allele in common (and preferably, are syngeneic), in which the antigenic cells have been treated according to the methods of the invention. The antigenic cells are treated by subjecting them to osmotic shock followed by irradiation. As a result, a subset of T cells are activated and mature into antigen-reactive cytotoxic T cells. The effectiveness of the procedure may be enhanced by repeated restimulations and/or the addition of heat shock protein-peptide complexes. Methods and compositions are also disclosed for the treatment and prevention in a subject of cancer or infectious disease comprising administering to the subject matched cytotoxic T cells that are generated in vitro by the present methods.

34 Claims, 4 Drawing Sheets

OTHER PUBLICATIONS

Valitutti et al., 1995, Nature 375:148–151.
Vanbuskirk et al., 1989, J. Exp. Med. 170:1799–1809.
Yewdell and Bennink, 1992, Adv. Immunol. 52:1–123.
Young, 1990, Ann. Rev. Immunol. 8:401–420.
Zarling et al., 1978, Nature 274:269–271.
Barrios et al., 1994, "Specificity of antibodies induced after immunization of mice with the mycobacterial heat shock protein of 65kD", Clin. Exp. Immunol., 98:224–228.

Barrios et al., 1994, "Heat shock protein as carrier molecules: in vivo helper effect mediated by *Escherichia coli* GroEL and DnaK proteins requires cross–linking with antigen", Clin. Exp. Immunol., 98:229–233.

Moore et al., 1988 "Introduction of soluble protein into the Class I pathway of Antigen processing and presentation", Cell 54:777–785.

# METHODS FOR GENERATING CYTOTOXIC T CELLS IN VITRO

This invention was made with government support under grant numbers CA44786 and CA64394 awarded by the National Institutes of Health. The government has certain rights in the invention.

TABLE OF CONTENTS

1. INTRODUCTION
2. BACKGROUND OF THE INVENTION
   2.1 IMMUNITY AND IMMUNIZATION
   2.2 THE IMMUNE RESPONSE
   2.3 ADOPTIVE IMMUNOTHERAPY OF CANCER
3. SUMMARY OF THE INVENTION
4. BRIEF DESCRIPTIONS OF DRAWINGS
5. DETAILED DESCRIPTION OF THE INVENTION
   5.1 SOURCES OF ANTIGENIC CELLS
   5.2 SOURCES OF IMMUNE CELLS
   5.3 GENERATION OF CYTOTOXIC T CELLS
   5.4 PURIFICATION OF HEAT SHOCK PROTEIN-PEPTIDE COMPLEXES
   5.5 DETERMINATION OF REACTIVITY OF RESPONDING T CELLS
   5.6 REINFUSION OF ANTIGEN-REACTIVE T CELLS
   5.7 TARGET INFECTIOUS DISEASES
   5.8 TARGET CANCERS
6. EXAMPLE
   6.1 MATERIALS
   6.2 PROCEDURE
   6.3 RESULTS

1. INTRODUCTION

The present invention relates to methods for generating antigen-reactive cytotoxic T cells for immunotherapy. The methods involve in vitro culture of immune cells with treated cancer cells or pathogen-infected cells, which results in the activation of a subset of T cells that are capable of effecting an antigen-specific cytotoxic T cell response.

2. BACKGROUND OF THE INVENTION

2.1 IMMUNITY AND IMMUNIZATION

The immune system protects a host against pathogens by mounting an immune response which is specific to an antigen of an invading pathogen. The objective of immunization is to elicit an early protective immune response by administering to the host an attenuated pathogen, or an antigen associated with a pathogen. This approach has been implemented successfully to prevent a variety of infectious diseases, such as polio, tetanus and diphtheria.

Immunization may be accomplished passively by administering either preformed immunoreactive serum or cells; or actively by presenting a suitable antigenic stimulus to the host's immune system.

Passive immunization is useful for a host who cannot produce antibodies, or for those who might develop disease before active immunization could stimulate antibody production. However, antibodies produced following some infections, particularly those due to mycobacteria, fungi, and many viruses, are not effective in protecting against the infection. Rather, the action of lymphocytes and macrophages largely determines recovery from these diseases.

Active immunization may be achieved with either viable or non-viable antigenic agents. Viable agents are generally preferred because the immune response provoked is more reliable and long-lived. However, viable vaccines may cause serious illness in an immunologically incompetent host, such as patients receiving corticosteroids, alkylating drugs, radiation or immunosuppressants. The use of attenuated strains always carries the risk that the attenuated agent may recombine with host DNA and mutate into a virulent strain. See generally, Ada, G. L., 1989, Chapter 36, in *Fundamental Immunology*, 2nd edition, ed. Paul W. E., Raven Press, New York, pp. 985–1032; Cohen, S. N., 1987, Chapter 37, in *Basic and Clinical Immunology*, 6th edition, ed. Stites, Stobo and Wells, Appleton and Lange, pp. 669–689.

2.2 THE IMMUNE RESPONSE

Cells of the immune system arise from pluripotent stem cells through two main lines of differentiation: a) the lymphoid lineage producing lymphocytes (T cells, B cells, natural killer cells), and b) the myeloid lineage (monocytes, macrophages and neutrophils) and other accessory cells (dendritic cells, platelets and mast cells). In the circulatory system and secondary lymphoid organs of an adult animal, lymphocytes recirculate and search for invading foreign substances. Pathogens and antigens tend to be trapped in secondary lymphoid organs, such as the spleen and the lymph nodes, where antigens are taken up by antigen-presenting cells (APC). Cell-mediated immune reactions require initial interaction between T cells and APC which trigger several effector pathways, including activation of cytotoxic T cells, and stimulation of T cell production of cytokines.

The process of presenting an antigen to T cells involves antigen capture by an APC, either by binding to a receptor or by uptake in the fluid phase. This is followed by proteolytic degradation of the antigen, and formation of a complex between antigenic peptide and major histocompatibility complex (MHC) molecules within the APC (Lanzavecchia, 1996, Curr. Opin. Immunol. 8:348–354). In pathogen-infected cells, proteins of the pathogens are degraded inside the cells, and some of the resulting peptides are transported into the lumen of the endoplasmic reticulum where they form complexes with class I MHC molecules. Additionally, antigens can be chaperoned by heat shock proteins into an endogenous pathway whereby antigenic peptides become associated with class I MHC molecules (Suto et al., 1995, Science 269:1585–1588; Srivastava et al., 1994, Immunogenetics 39:93–98). These peptide-MHC complexes are then transported to and accumulate on the cell surfaces, where they are recognized by receptors on T cells (Yewdell et al., 1992, Adv. Immunol. 52:1–123; Bevan, 1995, J. Exp. Med. 182:639–641).

Class I and Class II major histocompatibility complex (MHC) molecules are the most polymorphic proteins known. A further degree of heterogeneity of MHC molecule is observed at the level of haplotype or the combination of MHC Class I and II molecules encoded on a single chromosome. In the human, three distinct genetic loci designated, HLA-A, HLA-B and HLA-C, have been identified encoding class I molecules. Because the binding of T cell receptors are specific for a complex comprising an antigenic peptide and the polymorphic portion of the MHC molecule, T cells may not respond or respond poorly when an MHC molecule of a different genetic type is encountered. This specificity of binding results in the phenomenon of MHC-restricted T cell recognition and T cell cytotoxicity.

Cytotoxic T cells are antigen-specific effector cells that are important in resisting pathogens, cancer and allograft rejection. Most cytotoxic T cells are CD8+ cells that recognize antigen presented by MHC class I molecules which are expressed by almost all cell types. Cytotoxic T cells develop and undergo selection in the thymus, and then mature into functional cytotoxic T cells in the tissues after receiving two signals. The first signal is triggered by specific antigen-MHC complexes on the surface of antigen-presenting cells (APC). The second signal is provided by cytokines produced by CD4+ helper T cells, such as interferon-γ, and interleukin-2 (IL-2), interleukin-4 (IL-4), interleukin-7 (IL-7) and interleukin-12 (IL-12).

Cytotoxic T cells can kill target cells directly via two pathways (Berke, 1995, Cell 81:9; Taylor et al., 1992, Curr. Opin. Immunol. 4:338–343). One pathway involves secretion of performs, granzymes and serine esterases stored in specialized granules unique to cytotoxic T cells. A second mechanism involves the cross-linking of the Fas ligand on the cytotoxic T cell to Fas on the target cell which is then induced to undergo programmed cell death. The ability of cytotoxic T cells to kill target cells is restricted by antigenic and genetic factors. For lysis of target cells, the target cells must carry the same antigen that originally induced the activation of the cytotoxic T cells, and the same MHC class I molecule as the cytotoxic T cells.

2.3 ADOPTIVE IMMUNOTHERAPY OF CANCER

Studies with experimental animal tumors as well as spontaneous human tumors have demonstrated that many tumors do express antigens that can induce an immune response. Some antigens are unique to the tumor, and some are found on both tumor and normal cells. Several factors can greatly influence the immunogenicity of the tumor induced, including, for example, the specific type of carcinogen involved, and immunocompetence of the host and latency period (Old et al., 1962, Ann. N.Y. Acad. Sci. 101:80–106; Bartlett, 1972, J Natl Cancer Inst 49:493–504). It has been demonstrated that T cell-mediated immunity is of critical importance for rejection of virally and chemically induced tumors (Klein et al., 1960, Cancer Res. 20:1561–1572; Tevethia et al., 1974, J. Immunol. 13:1417–1423). The cytotoxic T cell response is the most important host response for the control of growth of antigenic tumor cells (Anichimi et al., 1987, Immunol. Today 8:385–389).

Adoptive immunotherapy of cancer takes the therapeutic approach, wherein immune cells with an antitumor reactivity are administered to a tumor-bearing host, with the objective that the cells cause either directly or indirectly, the regression of an established tumor. Immunization of hosts bearing established tumors with tumor cells or tumor antigens has generally been ineffective since the tumor is likely to have elicited an immunosuppressive response (Greenberg, P. D., 1987, Chapter 14, in *Basic and Clinical Immunology*, 6th ed., ed. by Stites, Stobo and Wells, Appleton and Lange, pp. 186–196). Thus, prior to immunotherapy, it has been necessary to reduce the tumor mass and deplete all the T cells in the tumor-bearing host (Greenberg et al., 1983, page 301–335, in "Basic and Clinical Tumor Immunology", ed. Herbermann RR, Martinus Nijhoff).

Animal models have been developed in which hosts bearing advanced tumors can be treated by the transfer of tumor-specific specific syngeneic T cells (Mulé et al., 1984, Science 225:1487–1489). Investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S.A., U.S. Pat. No. 4,690,914, issued Sep. 1, 1987; Rosenberg et al., 1988, N. Engl. J. Med., 319:1676–1680). For example, TIL expanded in vitro in the presence of IL-2 have been adoptively transferred to cancer patients, resulting in tumor regression in select patients with metastatic melanoma. Melanoma TIL grown in IL-2 have been identified as activated T lymphocytes CD+ HLA-DR+, which are predominantly CD8+ cells with unique in vitro antitumor properties. Many long-term melanoma TIL cultures lyse autologous tumors in a specific MHC class I- and T cell antigen receptor-dependent manner (Topalian et al., 1989, J. Immunol. 142:3714).

Application of these methods for treatment of human cancers would entail isolating a specific set of tumor-cancers reactive lymphocytes present in a patient, expanding these cells to large numbers in vitro, and then putting these cells back into the host by multiple infusions. Since T cells expanded in the presence of IL-2 are dependent upon IL-2 for survival, infusion of IL-2 after cell transfer prolongs the survival and augments the therapeutic efficacy of cultured T cells (Rosenberg et al., 1987, N. Engl. J. Med. 316:889–897). However, the toxicity of the high-dose IL-2 and activated lymphocyte treatment has been considerable, including high fevers, hypotension, damage to the endothelial wall due to capillary leak syndrome, and various adverse cardiac events such as arrhythmias and myocardial infarction (Rosenberg et al., 1988, N. Engl. J. Med. 319:1676–1680). Furthermore, the demanding technical expertise required to generate TILs, the quantity of material needed, and the severe adverse side effects limit the use of these techniques to specialized treatment centers.

Thus, it would be desirable to have a method for rapidly generating a large number of activated cytotoxic T cells to any antigen rapidly, which would have the convenience of in vitro culture, and not have the above-described risks or side-effects associated with active immunization.

3. SUMMARY OF THE INVENTION

The present invention relates to methods for generating antigen-reactive cytotoxic T cells that can be used for the prevention or treatment of a disease or disorder, such as infectious disease and cancer. The methods of the invention provide cytotoxic T cells that are capable of specifically killing antigenic cells, such as cancer cells or infected cells, with which the T cell has been primed.

The methods of the invention comprise subjecting live antigenic cells to osmotic shock, and then irradiation, and culturing of the treated antigenic cells with immune cells for a period of time sufficient for the priming of T cells in the immune cells. T cells that are primed (antigen-specific activated) by the method of the invention include naive T cells present among the immune cells. The methods of the invention for providing primed cytotoxic T cells are carried out in vitro and do not require immunization of the host with an antigen, thus reducing the risk of infections or immune disorders associated with immunization. The effectiveness of the in vitro priming reaction can be enhanced by the addition of heat shock protein-peptide complexes, e.g., isolated from the antigenic cells. The cytotoxic T cells provided by the methods of the invention can be administered in vivo, to provide a cell mediated immune response against the antigen to which they are primed.

The methods may further comprise restimulation of the primed T cells, such that a stable antigen-reactive T cell culture or T cell line can be maintained for extended periods in vitro. Therefore, T cells reactive to cancer cells and cells infected with a pathogen can be generated rapidly in large numbers in vitro for various therapeutic and prophylactic applications for cancer and diseases and disorders associated with infection by the pathogen, respectively. The antigen-reactive T cell culture or T cell line can be stored, and used to resupply cytotoxic T cells for long term use in vivo.

The present invention also encompasses methods of treatment or prevention in a subject of cancer or infectious disease comprising administering to the subject antigen-reactive cytotoxic T cells provided by the methods of the invention. In a preferred aspect, the methods of immunotherapy of the invention are autologous in that the immune cells (and optionally, also the antigenic cells) are isolated from the same subject (preferably, human) who receives the antigen-reactive cytotoxic T cells.

Cytotoxic T cells that are reactive to infected cells can be used to treat a variety of infectious diseases (those diseases associated with or caused by infection with the same infectious agent as that infecting the infected cells), including but not limited to acute viral infections and infections by opportunistic infectious pathogens in immunosuppressed or immunodeficient subjects. Cytotoxic T cells reactive to cancer cells may be used alone or in conjunction with administration of cytokines, surgery and/or chemotherapy in treatment aimed at achieving cancer regression and eradicating metastases.

5. DETAILED DESCRIPTION OF THE INVENTION

The present invention relates to methods for generating antigen-reactive cytotoxic T cells that can be used in the prevention or treatment of a disease or disorder, such as infectious disease and cancer. The inventors of the present invention discovered a method for priming T cells in vitro with antigenic cells such as cancer cells or infected cells, that leads to activation, proliferation and maturation of a specific set of antigen-reactive cytotoxic T cells. The cytotoxic T cells generated by the methods of the invention are capable of specifically killing or causing lysis of the cancer cells or infected cells, as the case may be, or any cells bearing the same antigens and similar MHC molecules with which the T cells are primed. The antigen-reactive T cells can be administered in vivo autologously (i.e., to the same individual from which the T cells (or parental cells to the T cells) were originally obtained) or sygeneically (i.e., to an identical twin of the individual from which the cancer or infected cells were initially obtained); or allogeneically to an individual who shares at least one common MHC allele with the individual from which the antigenic cells and T cells were originally obtained.

As used herein, the term "antigenic cells" refers to any cells, preferably cancer cells or infected cells, which can elicit an immune response in a subject. The sources of antigenic cells, and methods of preparation of antigenic cells for use in the present methods are discussed in section 5.1.

The "immune cells" that are contacted with the antigenic cells, and from which the cytotoxic T cells are generated, are a mixture of cells comprising T cells and antigen presenting cells. The antigenic presenting cells may be but are not limited to macrophages, dendritic cells, and/or B cells. The term "priming" as used herein is synonymous with the process of antigen-induced activation of T cells.

According to the invention, cellular immunotherapy is carried out by obtaining antigenic cells and immune cells from one or more, preferably the same subject, and activating of T cells within the immune cell population with the antigenic cells by the methods of the invention. This in vitro activation of T cells, followed by clonal expansion in cell culture of antigen-reactive cytotoxic T cells, and administration of the cytotoxic T cells into the subject constitute a useful therapeutic and prophylactic strategy. When infused into the subject, antigen-reactive cytotoxic T cells of the invention can specifically and directly kill target cells in vivo that bear the same antigen as the antigenic cells, thereby inhibiting cancer growth, or preventing or limiting the spread of the pathogen in the recipient.

In a preferred embodiment of the invention, the antigenic cells, the T cells, and the recipient of the cytotoxic T cells have the same MHC haplotype, i.e., the invention is directed to the use of autologous T cells stimulated in vitro with autologously-derived antigenic cells for the treatment or prevention of cancer or infectious disease in the same subject from which the T cells (or preferably, all the immune cells) and antigenic cells were originally derived. In a more preferred aspect, the immune cells and antigenic cells are isolated from a human subject in need of cellular immunotherapy.

In another embodiment of the invention, the T cells and the recipient have the same haplotype while the antigenic cells are allogeneic to the T cells and the recipient but matched at at least one MHC allele, i.e., antigenic cells are used to prime T cells, which T cells are then administered to a recipient from which the T cells were originally obtained, and in which the antigenic cells and the T cells share at least one but not all six MHC alleles.

In a least preferred embodiment of the invention, the antigenic cells, the T cells and the recipient are all allogeneic with respect to each other, but all have at least one common MHC allele shared among the antigenic cells, the T cells and the recipient.

According to the invention, the methods for generating cytotoxic T lymphocytes comprise subjecting live antigenic cells to osmotic shock, followed by irradiation, and culturing the immune cells with the mock-loaded antigenic cells. The term "mock-loading" as used herein refers to the treatment of antigenic cells with osmotic shock, followed by irradiation. The subjecting to osmotic shock, which is preferably by subjecting the cells first to a hyperosmotic (hypertonic) buffer (i.e., a buffer that is hyperosmotic (has a higher osmotic pressure) relative to physiologic conditions within a cell) and then a hypotonic buffer (i.e., a buffer that is hypotonic (has a lower osmotic pressure) with respect to physiologic conditions within a cell) is carried out such that the live antigenic cells do not rupture/lyse. As a result of changes in osmotic pressure, the antigenic cells undergo shrinkage and expansion but without rupture. After a period of time in culture, a subset of T cells in the immune cells are primed to react with antigens of the antigenic cells, and mature into antigen-reactive cytotoxic T cells.

Without limitation of the present invention to any particular scientific model or mechanism, the results described herein suggest that osmotically-shocked antigenic cells undergo fusion with macrophages (or other antigen presenting cells) present in the pool of immune cells, and that such fused cells are uniquely enabled to induce antigen-specific activation of T cells in vitro.

In another embodiment of the invention, the methods may further comprise restimulation of the primed immune cells comprising the cytotoxic T cells, by culturing the cells with feeder cells and irradiated antigenic cells, optionally in the presence of a composition comprising one or more cytokines (e.g., purified IL-2, Con A-stimulated spleen cell supernatant). In this manner, by restimulation from time-to-time, a stable antigen-specific T cell culture or cell line can be maintained in vitro for long periods of time. The T cell culture or cell line thus created can be stored, and if preserved (e.g., by formulation with a cryopreservative and freezing; or by lyophilization) used to resupply cytotoxic T cells at desired intervals for long term uses.

In yet another embodiment of the invention, the effectiveness of the in vitro priming reaction can be enhanced by inclusion in the in vitro priming reaction of noncovalent complexes of heat shock protein and antigenic protein/peptides either recovered from the antigenic cells, or prepared exogenously in which the peptide has the antigenicity of an antigen of interest of the antigenic cells. The heat shock protein-peptide complexes can also be added during restimulation.

According to a specific embodiment of the invention, antigen-reactive cytotoxic T cells can also be generated and used prophylactically to prevent infection, or development or remission of cancer. In another embodiment, such T cells can be used therapeutically to treat infection or its sequelae or to treat cancer. Preferably, the antigenic cells used to generate the T cells are syngeneic to the subject to which they are to be administered, e.g., are obtained from the subject. However, if cancer cells or pathogen-infected cells that are syngeneic to the subject are not available for use, the methods of the invention provide that such antigenic cells having the same MHC haplotype as the intended recipient of the cells can be prepared in vitro using noncancerous or uninfected cells (e.g., normal cells) collected from the recipient. For example, depending on the mode of transmission of the pathogen, normal cells obtained from the recipient can be infected in vitro by incubation with the pathogen or other pathogen-infected cells, and then used to prime the immune cells. In another embodiment, normal cells can be induced to become cancer cells, e.g., by treatment with carcinogens, such as chemicals and/or radiation or infection with a transforming virus, and then used to prime the immune cells. Furthermore, in another embodiment, if the cloned gene of the antigen of interest is available, normal cells from the subject can be transformed or transfected with the gene, such that the antigen of interest is expressed recombinantly in the cells, and then such cells can be used in the priming reaction. In a less preferred aspect, antigenic cells for use can be prepared from cells that are not syngeneic but that have at least one MHC allele in common with the intended recipient.

In an immune response, the process of antigen-induced T cell activation occurs in vivo typically in secondary lymphoid tissues, such as the lymph nodes and the spleen. By following the present methods, any antigenic cells of interest can be used to prime T cells or previously activated T cells in vitro, even cancer cells or infected cells that are considered unsafe for use in active immunization. Thus, one advantage of the present methods is that antigen-specific cytotoxic T cells can be generated in vitro against cancer cells or infected cells without having to immunize a subject with the antigenic cells or molecules.

There are many advantages of immunotherapy as provided by the present invention. Tumor bulk is minimal following surgery, and immunotherapy is most effective in this situation. In a specific embodiment, the preventive and therapeutic methods of the invention are directed at enhancing the immunocompetence of a cancer patient either before surgery or after surgery, and enhancing cell-mediated tumor-specific immunity against cancer cells, with the objective being inhibition of proliferation of cancer cells, and total eradication of residual cancer cells in the body. In another preferred aspect, cytotoxic T cells reactive against human cancer cells can be used, alone or in conjunction with surgery, chemotherapy, radiation or other anti-cancer therapies, to eradicate metastases or micrometastases, or to purge bone marrow of cancer cells during bone marrow transplantation. For example, to eradicate or inhibit the growth of metastases or micrometastases, the cytotoxic T cells provided by the invention are administered in vivo, to the subject having or suspected of having the metastases or micrometastases. For example, to purge bone marrow of cancer cells during bone marrow transplantation, bone marrow from the donor is contacted in vitro with the cytotoxic T cells provided by the invention, so that the cytotoxic T cells lyse any residual cancer cells in the bone marrow, prior to administering the bone marrow to the subject for purposes of hematopoietic reconstitution. The bone marrow transplantation is preferably autologous.

Moreover, if cancer patients undergo surgery with anesthesia, and subsequent chemotherapy, the resulting immunosuppression experienced by the patient may be lessened by cellular immunotherapy in the preoperative period, thereby reducing the incidence of infectious complications. There is also the possibility that tumor cells are shed into circulation at surgery, and thus, effective immunotherapy applied at this time can eliminate these cells in vivo. The invention thus provides a method of prophylaxis or treatment comprising administering to a cancer patient the cytotoxic T cells provided by the present invention, reactive against an antigen of the patient's cancer cells, prior to, during, and/or subsequent to surgery and/or chemotherapy undergone by the cancer patient.

In a preferred aspect involving acute viral infection of humans, cytotoxic T cells reactive against virus-infected cells of a human subject can be rapidly generated and reinfused back to the subject for controlling the viral infection. An effective specific cell-mediated response against viral-infected cells can be generated by the present methods in vitro in less time than when relying on the in vivo mechanisms of the subject's immune system.

In another preferred aspect, the invention provides cytotoxic T cells reactive against an opportunistic pathogen that infects immunosuppressed or immunodeficient subjects, such as but not limited to cytomegalovirus, *Toxoplasma gondii, Herpes zoster, Herpes simplex, Pneumocystis carinii, Mycobacterium avium-intracellulare, Mycobacterium tuberculosis*, Cryptosporidium, and Candida species. The cytotoxic T cells of the invention can be used therapeutically, and preferably autologously, in human patients suffering from acquired immunodeficiency syndrome (AIDS) and associated infections and cancers, or prophylactically in subjects that are infected with the human immunodeficiency virus (HIV), or HIV seropositive subjects or otherwise at high risk for developing AIDS.

5.1 SOURCES OF ANTIGENIC CELLS

The present invention provides methods for priming T cells in vitro with cancer cells or infected cells or other antigenic cells of interest. For treatment or prevention of cancer, the methods of the invention provide cytotoxic T cells primed against molecules (antigens) expressed by antigenic cells that will induce an immune response against the cancer cells or tumor, preferably human cancers, e.g., tumor-specific antigens and tumor associated antigens. For treatment or prevention of infectious diseases, the methods of the invention provide cytotoxic T cells primed against molecules (antigens) expressed by antigenic cells that will induce an immune response against host cells infected by the pathogen that causes the infectious disease or against the pathogen, including but not limited to, viruses, bacteria, fungi, protozoans, parasites, etc., and preferably pathogens that infect humans. Since whole cancer cells or infected cells or other antigenic cells are used in the present methods, it is not necessary to isolate or characterize or even know the identities of these antigens in advance of using the present methods.

In various embodiments, any cell bearing an antigen can be used in the present methods for in vitro priming of MHC-matched T cells. It is not essential to use cells of the ultimate target cells in vivo (e.g., of the tumor or infected cells of the intended recipient that it is desired to inhibit) to prime the T cells, so long as the antigen(s) on the target cells is present on the cells used in priming the T cells. As described above, the antigenic cells used in priming, the T cells, and the target cells must have at least one common MHC allele in order for effective priming and cytotoxic activity of T cells. The more MHC alleles in common, the more preferred the method. Most preferred is where the T cells and antigenic cells are derived from the intended recipient (i.e., all are autologous). Less preferred is where the T cells are autologous to the recipient, and where the antigenic cells are nonautologous (but share at least one MHC allele with the T cells). Least preferred is where neither the T cells or antigenic cells are autologous to the recipient, but the T cells, antigenic cells, and recipient all have at least one MHC allele in common. If the antigenic cells, T cells and target cells are obtained from the same or syngeneic individual, such cells will all have the same MHC haplotype. If all are not obtained from the same subject, and it is not known and it is desired to assess whether the antigenic cells, T cells, and/or target cells have the same MHC haplotype or any MHC alleles in common, such can be determined by standard HLA typing techniques well known in the art, such as serological tests and DNA analysis of the MHC loci. Such a determination of MHC haplotype need not be undertaken prior to carrying out the mock-loading and priming methods of the invention; one may simply carry out such methods and the obtaining of the desired cytotoxic activity indicates that the matching MHC alleles were present.

The source of the antigenic cells may be selected, depending on the nature of the disease with which the antigen is associated, and the intended use of the resulting cytotoxic T cells. In one embodiment of the invention, any tissues, or cells isolated from a cancer, including cancer that has metastasized to multiple sites, can be used in the present method. For example, leukemic cells circulating in blood, lymph or other body fluids can also be used, solid tumor tissue (e.g., primary tissue from a biopsy) can be used. Examples of cancers that are amenable to the methods of the invention are listed infra.

In another embodiment of the invention, any cell that is infected with a pathogen, in particular, an intracellular pathogen, such as a virus, bacterium, fungus, parasite, or protozoan, can be used. An exemplary list of infectious diseases that can be treated or prevented by cytotoxic T cells of the invention is provided below.

Cell lines derived from cancer tissues, cancer cells, or infected cells can also be used as antigenic cells, provided that the cells of the cell line have the same antigenic determinant(s) as the antigen of interest on the antigenic cells. Cancer or infected tissues, cells, or cell lines of human origin are preferred.

Cancer cells or infected cells can be identified and isolated by any method known in the art. For example, cancer cells or infected cells can be identified by morphology, enzyme assays, proliferation assays, or the presence of pathogens or cancer-causing viruses. If the characteristics of the antigen of interest are known, antigenic cells can also be identified or isolated by any biochemical or immunological methods known in the art. For example, cancer cells or infected cells can be isolated by surgery, endoscopy, other biopsy techniques, affinity chromatography, and fluorescence activated cell sorting (e.g., with fluorescently tagged antibody against an antigen express by the cells).

If the number of antigenic cells obtained from a subject is insufficient, the cells may be cultured in vitro by standard methods to expand the number of cells prior to use in the present methods. There is no requirement that a clonal or homogeneous or purified population of antigenic cells be used to prime the T cells. A mixture of cells can be used provided that a substantial number of cells in the mixture contain the antigen of interest. In a specific embodiment, the antigenic cells and/or immune cells are purified.

In another embodiment of the invention, antigen-reactive T cells are generated for prophylaxis against cancer or infectious disease. In this instance, the appropriate autologous antigenic cells may not exist, since the recipient of the cytotoxic T cells may not have the cancer or the infectious disease. Moreover, in an embodiment wherein the T cells are used for prophylaxis, desired quantities of autologous antigenic cells may not be obtainable from the recipient. In such instances, a source of antigenic cells having at least one common MHC allele, or preferably the same MHC haplotype as the recipient, which is used to prime the cytotoxic T cells, can be prepared in vitro from noncancerous or uninfected cells (e.g., normal cells), as appropriate, obtained from the recipient or other individual sharing at least one MHC allele with the recipient.

In order to prepare suitable antigenic cells that are cancer cells, noncancerous cells, preferably of the same cell type as the cancer desired to be inhibited can be isolated from the recipient or, less preferably, other individual who shares at least one MHC allele with the intended recipient, and treated with agents that cause the particular or a similar cancer or a transformed state; such agents may include but not limited to, radiation, chemical carcinogens, and viruses. Standard techniques can be used to treat the cells and propagate the cancer or transformed cells so produced.

In order to prepare pathogen-infected cells, uninfected cells of a cell type susceptible to infection by the pathogen can be infected in vitro with the pathogen that causes the disease. Depending on the mode of transmission and the biology of the pathogen, standard techniques can be used to facilitate infection by the pathogen, and propagation of the infected cells. For example, influenza viruses may be used to infect normal human fibroblasts; and mycobacteria may be used to infect normal human Schwann cells.

Alternatively, if the gene encoding a tumor-specific antigen, tumor-associated antigen or antigen of the pathogen is available, normal cells of the appropriate cell type from the intended recipient or an individual having at least one common MHC allele may be transformed or transfected in vitro with an expression construct containing the gene such that the antigen is expressed in the recipient's cells. Optionally, more than one such antigen may be expressed in the recipient's cell in this fashion, as will be appreciated by those skilled in the art, any techniques known, such as those described in Ausubel et al. (1989, Current Protocols in Molecular Biology, Wiley Interscience), may be used to perform the transformation or transfection and subsequent recombinant expression of the antigen gene in recipient's cells. These antigenic cells bearing one or more MHC molecules in common with the recipient are suitable for use in the in vitro priming reactions of the invention.

5.2 SOURCES OF IMMUNE CELLS

The immune cells used for priming according to the present invention, comprise a mixture of living cells of lymphoid and myeloid lineages, wherein the lymphoid cells comprise T cells that can be activated to differentiate into $CD4^+$ helper T cells and $CD8^+$ cytotoxic T cells, and wherein the myeloid cells comprise antigen-presenting cells (e.g., macrophages) that are functional in antigen-induced T cell activation. Preferably, the T cells have the same MHC haplotype as the antigenic cells and the target cells in the recipient.

Immune cells can be collected or isolated from blood, or secondary lymphoid organs of the subject, such as but not limited to lymph nodes, tonsils, the spleen, Peyer's patch of the intestine, and bone marrow, by any of the methods known in the art. Immune cells obtained from such sources typically comprise predominantly recirculating lymphocytes and macrophages at various stages of differentiation and maturation. optionally, standard techniques, such as morphological observation and immunochemical staining, can be used, if desired, to verify the presence of the desired cells, e.g., T cells, and macrophages. In a preferred aspect, the immune cells used in the in vitro methods of the invention are human peripheral blood compositions lacking red blood cells, e.g., whole blood leukocytes (whole peripheral blood from which the red blood cells and serum have been substantially removed), which can be collected from a human subject by standard techniques, such as by use of a syringe to withdraw the blood, followed by subjecting the blood to Ficoll-Hypaque (Pharmacia) gradient centrifugation. Blood, anticoagulated with preservative-free heparin, usually yields 0.5 to $1 \times 10^6$ lymphocytes/ml. Separated blood cells (e.g., leukocytes) may be frozen by standard techniques prior to use in the present methods. In a specific embodiment, the immune cells used are purified white blood cells comprising lymphocytes and macrophages.

T cells and antigen presenting cells, such as macrophages, can be obtained together, or separately (and then combined for use in the priming reaction), or optionally purified by any of various methods known in the art. In a preferred aspect human macrophages obtained from human blood cells are used. By way of example but not limitation, macrophages can be obtained as follows:

Mononuclear cells are isolated from peripheral blood of a patient (preferably the patient to be treated), by syringe removal of blood followed by Ficoll-Hypaque gradient centrifugation. Tissue culture dishes are pre-coated with the patient's own serum or with AB+ human serum and incubated at 37° C. for 1 hr. Non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF).

5.3 GENERATION OF CYTOTOXIC T CELLS

Antigen-reactive cytotoxic T cells are generated in vitro by activation and proliferation of a subset of T cells according to the methods described herein. After sufficient time is given for the in vitro priming reaction to occur, the T cells can be tested for cytotoxicity, restimulated to enhance or sustain the cytotoxicity, or stored or maintained in long-term culture for later use.

Any antigenic cell, e.g., cancer or infected cells described in section 5.1, may be used in the present methods. Typically, by way of example but not limitation, cancer cells can be isolated from a tumor that is surgically removed from a human patient who will be the recipient of the cytotoxic T cells. Prior to use, solid cancer tissue, pathogen-infected tissue or aggregated cancer cells should be dispersed, preferably mechanically, into a single cell suspension by standard techniques. Enzymes, such as but not limited to, collagenase and DNase may also be used to disperse cancer cells. Typically, approximately two to three million antigenic cells are used per priming reaction in the method. Thus, if necessary, the cancer or infected cells may be cultured by standard techniques under growth conditions in vitro to obtain the desired number of cells prior to use. Primary tissue or cell lines can be used.

The present invention provides a method for generating cytotoxic T cells comprising the following steps in the order stated: subjecting live antigenic cells to osmotic shock in vitro; subjecting the antigenic cells to irradiation in vitro;

culturing the antigenic cells with immune cells comprising T cells and antigen presenting cells in vitro, wherein the antigenic cells and T cells have at least one common MHC allele, such that cytotoxic T cells are generated.

According to the invention, the antigenic cells are subjected to an osmotic shock, which consists of incubating the antigenic cells first in a hyperosmotic (hypertonic) buffer, and then in a hypotonic buffer. A hyperosmotic or hypertonic buffer has a higher osmotic pressure relative to the physiological osmotic pressure of a cell. A hypotonic buffer has a lower osmotic pressure than the physiological osmotic pressure in a cell. The physiological osmotic pressure of a cell is that exerted by 0.155 M sodium chloride, which is equivalent to the osmotic pressure of a solution having 0.31 M sucrose (unlike sucrose, sodium chloride dissociates into two ions; the number of solute particles per unit volume determines the osmotic pressure).

The equation relating osmotic pressure of a solution to solute concentration may be written as $\pi=MRT$, wherein $\pi$=osmotic pressure, M=molarity of solute particles in moles of solute particles per liter solvent, R=gas constant and T=temperature in $°K$.

Any solutes, buffer systems and procedures that can be used to subject antigenic cells to a change in osmotic pressure can be used in the present methods. The hyperosmotic and hypotonic buffers, and time and temperature of incubations are chosen such that the cells are not ruptured. It is preferred that the temperature of incubation in both the hyperosmotic buffer and the hypotonic buffer is 37° C. It is further preferred that the osmotic pressure of the hyperosmotic buffer in which the antigenic cells are incubated falls within the range of 2 to 5 times, and is most preferably about three times, that of the physiological osmotic pressure. It is also preferred that the final osmotic pressure of the hypotonic solution in which the antigenic cells are incubated falls within the range of 0.2 times to 0.9 times (preferably 0.5 to 0.75 times), and is most preferably about two-thirds, that of the physiological osmotic pressure.

When the cell is placed in a hyperosmotic buffer, the chemical potential of water in the cell is more than outside, and water flows out of the cell. In hypotonic media, the flow goes in the other direction with water entering the cell. As a result of the change in osmotic pressure, the antigenic cells undergo first shrinkage and then expansion but without rupture of the cells. The osmotically-shocked antigenic cells are then irradiated.

A preferred and exemplary, non-limiting protocol for carrying out the osmotic shock and irradiation is provided hereinbelow:

The cancer or infected cells (e.g., $2 \times 10^6$ cells) are incubated at 37° C. for 5 to 60 minutes in a hyperosmotic buffer (0.5 ml per $2 \times 10^6$ cells) containing 0.5 M sucrose, 10% w/v polyethylene glycol 1000, 10 mM HEPES in tissue culture medium, such as RPMI 1640. (Alternatively, any solutes can be used to prepare a hyperosmotic buffer that would exert a similar osmotic pressure, e.g., about three times physiologic osmotic pressure.) In order to reverse the osmotic effect rapidly, the medium containing the cells is diluted by adding 30 times the volume of a hypotonic buffer (15 ml per $2 \times 10^6$ cells) consisting of 60% tissue culture medium in water. The cells are then incubated at 37° C., e.g., for 1–10 minutes, before they are collected by centrifugation at 500–5000 rpm in a standard laboratory centrifuge. The antigenic cells are not ruptured at the end of this process. The osmotically-shocked antigenic cells are resuspended in culture medium (5 ml for $2 \times 10^6$ cells) and allowed to recover for 0.5 to 24 hours at 37° C., 5% $CO_2$.

After the osmotic shock, the antigenic cells (e.g., one to two million) are irradiated with 1,000 to 10,000 rads in culture medium containing 5% fetal calf serum, and then washed in culture medium containing 10% fetal calf serum. For example, the antigenic cells are irradiated for 30 minutes using a Gammator 50 set to deliver 800 rads/min. Antigenic cells that are subjected to osmotic shock, followed by irradiation are referred to herein as mock-loaded antigenic cells. The in vitro priming reaction is carried out by culturing the mock-loaded cells with an immune cell composition comprising T cells and antigen presenting cells of a subject. As described in section 5.2, immune cells can be obtained from the spleen or preferably, peripheral blood. If lymphoid tissues or organs are used as a source of immune cells, it is preferable to disperse the cells so as to form a single cell suspension prior to use.

A preferred and exemplary, non-limiting protocol for carrying out the in vitro priming reaction is provided hereinbelow:

Approximately $1 \times 10^6$ cancer or infected cells treated as described above (with osmotic shock and irradiation) are used to prime $1 \times 10^8$ immune cells (e.g., whole blood from which the red blood cells and serum have been removed). The cells are mixed and co-cultured at 37° C., 5% $CO_2$, for preferably 3–9 days, preferably in multiwell plates. The ratio of treated cells to immune cells in the mixed cell culture is preferably 1:100, and may be adjusted to optimize the ratio for generation of responding cytotoxic T cells, after measuring the resulting reactivity of the responding cytotoxic T cells at various ratios. Optionally, noncovalent complexes of heat shock protein and peptides isolated from cells that are the same as the antigenic cells, or noncovalent complexes of heat shock protein and exogenous antigenic peptides, are added to the mixed cell culture to enhance the efficiency of the in vitro priming reaction. Heat shock protein-peptide complexes can be isolated or prepared in vitro by methods described in the next section. A concentration range of 1–50 μg heat shock protein peptide complex per ml culture medium is preferred. After several days in culture, e.g., on day six, a $^{51}Cr$ release assay or any other suitable assay known in the art may be performed if desired, to test for cytotoxic T cell activity in the mixed cell culture.

Any methods known in the art may be used to maintain the responding T cell clones. Culture medium for mouse cells usually includes fetal calf serum (FCS) at concentrations ranging from 2 to 10% and 2-mercaptoethanol, usually at $5 \times 10^{-5}$ M. Human cell cultures are usually prepared in medium containing 10 to 20% pooled human serum, although FCS at 10% is an adequate substitute for pooled human serum. Antibiotics, usually penicillin (100 μg/ml) and streptomycin (100 U/ml), may be used. HEPES (25 mM) or morpholinopropane-sulfonic acid (MOPS) (10 mM) can be used to buffer the medium. Suitable culture media and conditions are well known in the art.

To enhance or sustain cytotoxic activity of the activated T cells, the mixed cell culture can optionally be restimulated with antigenic cells in the presence of feeder cells after many days in culture, for example, on day 9 or 10. The antigenic cells used for restimulation need not be osmotically shocked, but should be irradiated. Optionally, primed T cells (which are substantially suspended in the culture medium) can be recovered from the mixed cell culture by centrifugation of the culture medium, and restimulated by incubation with freshly irradiated antigenic cells in fresh culture medium at any of various responding T cell/antigenic cell ratios, such as, for example, 100:1. The incubation is preferably also in the presence of lymphokine(s), e.g., purified IL-2 and/or concanavalin A (con A)—stimulated spleen cell supernatant or conditioned medium from activated T cell culture. Preferably, human IL-2 is used with human cells. By repeated stimulations for example, carried out every 3 to 9 days, a continuous antigen-reactive T cell culture or T cell line with specificity for the antigens present on the antigenic cells can be maintained or established. Standard methods of T cell cloning and clonal expansion may be applied to further propagate these antigen-reactive T cells. See generally Fathman et al., 1989, in Chapter 30, in "Fundamental Immunology" 2nd edition, ed. Paul, W. E., Raven Press, New York, pp 803–815. The cells can be tested for reactivity on day six after restimulation.

Feeder cells can be any MHC haplotype-matched immune cells, preferably comprising antigenic presenting cells, or less preferably allogeneic immune cells sharing at least one MHC allele with the immune cells, and are typically obtained from peripheral blood leukocytes or the spleen by standard techniques. The feeder cells are preferably irradiated prior to use.

Spleen cells stimulated with concanavalin A (Con A SF) yield culture supernatants containing rather high levels of IL-2. By way of example, to prepare rat Con A SF, rat spleen cells are cultured at a density of $1.25 \times 10^6$ cells/ml in medium (DMEM, RPMI, or other suitable medium) containing 2 to 10% fetal calf serum (FCS) and $5 \times 10^{-5}$ M 2-mercaptoethanol. Con A (Pharmacia Fine Chemicals, Inc., Uppsala, Sweden) is added to give a final concentration of 2.5 to 5 µg/ml. After 48 hr, the culture supernatant is collected and centrifuged. Lymphokines other than IL-2, including colony stimulating factor and growth factors for B cells, may also be present as well in Con A SF. Such supernatants are useful for the initial cloning of T cells and for maintaining cloned T cells.

Recombinant human or murine IL-2 can be purchased commercially. Also, by way of example, human IL-2 can be prepared by culturing peripheral blood leukocytes or spleen cells ($5 \times 10^6$ per ml) in RPMI 1640 supplemented as above with PHA-P (Difco Laboratories, Detroit, Mich.) at a final concentration of 0.2%. IL-2-containing supernatant is collected by centrifugation after culture for 48 hr.

T cell cultures or cloned T cells primed by the methods of the invention can be stored frozen in liquid nitrogen for at least several years. For example, T cells, preferably during the early log phase of growth, are centrifuged and resuspended in medium containing 10% dimethyl sulfoxide (DMSO) at 4° C. Survival of frozen cells is probably greater if the serum concentration of the medium is at least 10%. For example, briefly, 24 hr after antigen exposure, T cells are harvested and resuspended in pre-cooled RPMI supplemented with 20% FCS and 10% dimethyl sulfoxide. By way of example, cells are frozen at a rate of approximately 1° C. per minute by placing them in a styrofoam box in a −70° C. Revco freezer. Such frozen cells should preferably be stored in liquid nitrogen.

For maintenance, T cell clones of interest can be expanded in multiwell plates and subsequently in tissue culture flasks. Briefly, by way of example and not limitation, for expansion, cells are harvested at intervals of 10 to 14 days, readjusted to $1 \times 10^5$ T cells/ml, and restimulated in the presence of feeder cells with newly irradiated antigenic cells and 10 units IL-2/ml. Cells are fed with fresh medium containing IL-2 every 5 days. Unlike macrophages which are adherent to the plates, T cells are non-adherent and can be substantially separated from macrophages by collecting the cell culture medium. Occasionally, cells grow rapidly and require repeated splitting when cell density exceeds $5 \times 10^5$ per ml.

5.4 PURIFICATION OF HEAT SHOCK PROTEIN-PEPTIDE COMPLEXES

In an embodiment wherein heat shock protein (hsp)-peptide complexes isolated from antigenic cells are desired to be added to the mixed cell culture, the hsps that can be used include but are not limited to, hsp70, hsp90, and gp96, alone or in combination. Preferably, the hsps are human hsps.

Heat shock proteins, which are also referred to interchangeably as stress proteins, useful in the practice of the instant invention can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties.

Any methods known in the art can be employed to purify endogenous hsp-peptide complexes from antigenic cells, e.g., cancer cells or infected cells, for use in the present methods. For example, the purification of hsp70-peptide complexes has been described previously, see, for example, Udono et al., 1993, J. Exp. Med. 178:1391–1396. See also International Publication No. WO 95/24923 dated Sep. 21, 1995.

Another method that can be applied for the purification of heat shock protein-peptide complexes, such as hsp70-peptide complexes, comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). Thus, hsp70-peptide complexes can be readily obtained from cancer cells or cells infected by an infectious agent or other cells by a rapid, one-step ADP-agarose chromatography. For example, Meth A sarcoma cells (500 million cells) can be homogenized in hypotonic buffer and the lysate is centrifuged at 100,000 g for 90 minutes at 4° C. The supernatant is applied to an ADP-agarose column. The columns are washed in buffer and are eluted with 3 mM.

These protocols may be used to isolate hsps from any eukaryotic cells, for example, tissues, isolated cells or immortalized eukaryotic cell lines infected with a pathogen, tumor cells or tumor cell lines, and eukaryotic cells transfected with a gene encoding and expressing a tumor-specific antigen, tumor-associated antigen or an antigen of the pathogen.

Furthermore, antigenic molecules, either purified from natural sources or chemically synthesized or recombinantly produced, may be reconstituted with a variety of naturally purified or chemically synthesized or recombinantly produced heat shock proteins in vitro to generate immunogenic noncovalent heat shock protein-peptide molecule complexes. A preferred, exemplary protocol for noncovalently complexing a stress protein and an exogenous antigenic molecule in vitro is described below.

Prior to complexing, the hsps are pretreated with ATP or low pH to remove any peptides that may be associated with the hsp of interest. When the ATP procedure is used, excess ATP is removed from the preparation by the addition of apyranase as described by Levy et al., 1991, Cell 67:265–274. When the low pH procedure is used, the buffer is readjusted to neutral pH by the addition of pH modifying reagents.

The antigenic molecules (1 µg) and the pretreated hsp (9 µg) are admixed to give an approximately 5 antigenic molecule:1 stress protein molar ratio. Then, the mixture is incubated for 15 minutes to 3 hours at room temperature in a suitable binding buffer such as one containing 20 mM sodium phosphate, pH 7.2, 350 mM NaCl, 3 mM MgCl$_2$ and 1 mM phenyl methyl sulfonyl fluoride (PMSF). The preparations are centrifuged through Centricon 10 assembly (Millipore) to remove any unbound peptide. The association of the peptides with the stress proteins can be assayed by sodium dodecyl sulfate-polyacrylamide gel electrophoresis (SDS-PAGE).

Alternatively, for producing complexes of hsp70 to exogenous antigenic molecules that are proteins, in a preferred embodiment, that 5–10 micrograms of purified hsp is incubated with equimolar quantities of the antigenic molecule in 20 mM sodium phosphate buffer pH 7.5, 0.5 M NaCl, 3 mM MgCl$_2$ and 1 mM ADP in a volume of 100 microliter at 37° C. for 1 hr. This incubation mixture is further diluted to 1 ml in phosphate-buffered saline.

Alternately, for producing complexes of gp96t or hsp90 to peptides, in a preferred embodiment, 5–10 micrograms of purified gp96 or hsp90 is incubated with equimolar or excess quantities of the antigenic peptide in a suitable buffer such as one containing 20 mM sodium phosphate buffer 7.5, 0.5 M NaCl, 3mM MgCl$_2$ at 60–65° C. for 5–20 minutes. This incubation mixture is allowed to cool to room temperature and centrifuged more than once if necessary through Centricon 10 assembly (Millipore to remove any unbound peptide).

Heat shock protein-peptide complexes isolated from antigenic cells or produced in vitro can be added directly to the mixed cell culture of antigenic cells and immune cells, preferably in the range of 1–50 µg/ml culture medium final concentration, during the initial in vitro priming reaction, and/or during any of the subsequent restimulation steps.

5.5 DETERMINATION OF REACTIVITY OF RESPONDING T CELLS

In an optional procedure, after the in vitro priming reaction, the mixed cell culture comprising responding T cells including the cytotoxic T cells of the invention can be assayed for reactivity using a $^{51}$Cr release assay, a cytokine assay, or any assay known in the art for measuring reactivity of immune effector cells.

By way of example but not limitation, the following four (4) hour $^{51}$Cr-release assay can be used (see, Palladino et al., 1987, Cancer Res. 47:5074–5079 and Blachere et al., 1993, J. Immunotherapy 14:352–356). In this assay, cells in the primed immune cell culture, i.e., the effector cells, are added to a target cell suspension to give various effector:target (E:T) ratios (usually from 1:1 to 40:1). The target cells are prelabelled by incubating 1×10$^6$ target cells in culture medium containing 200 MCi $^{51}$Cr/ml for one hour at 37° C. The labelled cells are washed three times following labeling. Each assay point (E:T ratio) is performed in triplicate. The controls measure spontaneous $^{51}$Cr release wherein no lymphocytes are added to the assays, and 100% release wherein the labelled target cells are lysed with detergent, such as TNEN (10 mM Tris-HCl, 250 mM NaCl, 0.1 mM EDTA and 1% NP-40). After incubating the effector/target cell mixtures for 4 hours, the cells are collected by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

$$\% \text{ cytotoxicity} = \frac{cpm \text{ of test sample minus } cpm \text{ of spontaneous } ^{51}Cr \text{ release}}{cpm \text{ of maximal } ^{51}Cr \text{ release minus } cpm \text{ of spontaneous } ^{51}Cr \text{ release}}$$

Alternatively, the reactivity of the responding T lymphocytes can also be determined by measuring the levels of cytokines, such as but not limited to tumor necrosis factor, granulocyte-macrophage colony stimulating factor, and interleukin-2, secreted upon stimulation.

5.6 REINFUSION OF ANTIGEN-REACTIVE T CELLS

The cytotoxic T cells of the invention, are infused into a recipient systemically, preferably intravenously, by conventional clinical procedures. In a specific embodiment, the immune cell population that was suspended in the culture medium is administered to the patient. Alternatively and optionally, cytotoxic T cells can be purified prior to administration by any standard methods, such as but not limited to, density gradient centrifugation, and affinity chromatography using an immobilized antibody to the CD8 antigen present on cytotoxic T cells. The antigen-reactive cytotoxic T cells are infused, preferentially by systemic administration into the recipient. Recipients generally receive from about 10$^6$ to about 10$^{12}$ of an immune cell composition (e.g., comprising nonadherent cells from the mixed cell culture) per administration or about 10$^5$ to about 10$^{11}$ purified cytotoxic T cells (or a composition comprising the same) per administration, and preferably about 10$^6$ to about 10$^8$ immune cells per administration or about 10$^5$ to about 10$^7$ purified cytotoxic T cells (or a composition comprising the same) per administration, depending on the condition of the patient. Preferably, such T cells are administered to an autologous recipient.

The subject or recipient is preferably an animal, including but not limited to animals such as cats, dogs, cows, pigs, mice, rats, monkeys, chickens, etc., and is preferably a mammal, and most preferably human.

Various delivery systems are known and can be used to administer the cytotoxic T cells of the invention, e.g., encapsulation in liposomes, microparticles, microcapsules. Methods of introduction include but are not limited to intradermal, intramuscular, intraperitoneal, intravenous, subcutaneous, intranasal, and oral routes. The cells may be administered by any convenient route, for example by infusion, and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer or infection, or directly into the cancer or tumor.

The present invention also provides pharmaceutical compositions. Such compositions comprise a therapeutically or prophylactically effective amount of cytotoxic T cells of the invention, and a pharmaceutically acceptable carrier or excipient. Such a carrier includes but is not limited to saline, culture medium with or without serum, buffered saline, dextrose, water, glycerol, ethanol, and combinations thereof. The carrier and composition can be sterile. The formulation should suit the mode of administration. The composition, if desired, can also contain minor amounts of wetting or emulsifying agents, or pH buffering agents.

In a preferred embodiment, the composition is formulated in accordance with routine procedures as a pharmaceutical composition adapted for intravenous administration to human beings. Typically, carriers for intravenous administration are sterile isotonic aqueous buffers. Where necessary, the composition may also include a local anesthetic such as lignocaine to ease pain at the site of the injection. Where the composition is to be administered by infusion, it can be dispensed with an infusion bottle containing sterile pharmaceutical grade water, saline or culture medium. Where the composition is administered by injection, an ampoule of sterile water or saline or culture medium for injection can be provided so that the ingredients may be mixed prior to administration.

The amount of cytotoxic T cells of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In some regimens, patients may optionally receive in addition a suitable dosage of a biological response modifier including but not limited to the interferon-T, interferon-α, interleukin-2, interleukin-4, interleukin-7, interleukin-10, interleukin-12, tumor necrosis factor, granulocyte-macrophage colony stimulating factor, or other cytokines and growth factors.

5.7 TARGET INFECTIOUS DISEASES

Infectious diseases that can be treated or prevented by cytotoxic T cells of the present invention are caused by infectious agents including, but not limited to viruses, bacteria, fungi, protozoans and parasites.

Viral diseases that can be treated or prevented by the methods and compositions of the present invention include, but are not limited to, those caused by hepatitis type A, hepatitis type B, hepatitis type C, influenza, varicella, adenovirus, *herpes simplex* type I (HSV-I), *herpes simplex* type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Bacterial diseases that can be treated or prevented by the methods and compositions of the present invention are caused by bacteria including, but not limited to, *mycobacteria rickettsia*, mycoplasma, neisseria and legionella.

Protozoal diseases that can be treated or prevented by the methods and compositions of the present invention are caused by protozoa including, but not limited to, leishmania, kokzidioa, and trypanosoma.

Parasitic diseases that can be treated or prevented by the methods and compositions of the present invention are caused by parasites including, but not limited to, chlamydia and rickettsia.

5.8 TARGET CANCERS

Cancers that can be treated or prevented by cytotoxic T cells and methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In a specific embodiment, the cancer is metastatic. In another specific embodiment, the cancer is a tumor. In yet another embodiment, the recipient has undergone autologous bone marrow transplantation as a part of cancer therapy.

6. EXAMPLE

The following example demonstrates the methods of the present invention for generating cytotoxic T cells in vitro, using four different types of cancer cells in two different mouse strains.

6.1 MATERIALS

Hyperosmotic buffer:

(0.5 ml per 2×10⁶ cells) 0.5 M sucrose (Baker Analyzed) 10% w/v Polyethylene glycol 1000 (Sigma) 10 mM HEPES buffer (Life Technologies) Plain RPMI 1640 (GIBCO BRL Life Technologies)

Hypotonic buffer:

(15 ml per 2×10⁶ cells) 3:2 ratio of Plain RPMI (GIBCO BRL Life Technologies) to Distilled Water Rat Con A was obtained by culturing rat spleen cells with 5 mg/ml of Concanavalin A as the mitogen for 24 hrs. After the rat cells were separated by centrifugation, the supernatant was used as rat Con A.

The following cancer cells were used: SVB6, a C57BL/6 mouse cancer cell line transformed with SV40 viruses); EL4 (a C57BL/6 mouse thymoma cell line); EG7 and N1 (mouse thymoma cell lines derived EL4); PS-C3H (a SV40-transformed C3H-He mouse sarcoma cell line) and UV6138 (a C3H-He mouse cancer cell line).

6.2 PROCEDURE

Two to three million cancer cells were resuspended in 0.5 ml of the hyperosmotic buffer and incubated for ten minutes at 37° C. To reverse the osmotic effect, the hypotonic buffer (15 ml) was added directly to the cells in the hyperosmotic buffer, and incubated for three more minutes at 37° C. The cells were immediately spun down in a standard laboratory centrifuge at 700 g at 4° C. The supernatant was poured off through a gauze pad (Johnson and Johnson Products Inc.) and the cells resuspended in 5 ml RPMI 1640 supplemented with 5% fetal calf serum (FCS), 1% glutamine, 1% penicillin-streptomycin, 1% nonessential amino acids, pyruvate and 0.1% 2-mercaptoethanol. The cells were allowed to recover for two hours at 37° C. and 5% $CO_2$.

One to two million of the treated cancer cells were irradiated (Gammator 50; 800 rads/min) for 30 minutes in 3 ml of complete RPMI 1640 containing 5% FCS. The cells were washed once and resuspended in complete RPMI 1640 containing 10% FCS.

The spleen from a naive mice was used to generate a single cell suspension in complete RPMI 1640 containing 5% FCS in a petri dish. The spleen cells were passed through a sterile 40 μm nylon strainer (Becton Dickinson), and centrifuged at 700 g–2500 g in a standard laboratory centrifuge, 4° C. The spleen cells (1×10⁸) were washed once in 10 ml of complete RPMI 1640 with 5% FCS, and plated out in a 24-well plate (1×10⁸ spleen cells per 24 wells; Becton Dickinson).

The treated cancer cells were added to each well so that each well had a total volume of 2 ml. Approximately a total of 1×10⁶ treated cancer cells were used to prime a total of 1×10⁸ spleen cells. The plates were incubated at 37° C. and 5% $CO_2$ for six days. A ⁵¹Cr release assay was performed on day six to test for T cell reactivity as follows: Target cells were labeled by incubation in $^{51}Cr$ for 60 min at 37° C., and washed three times in RPMI 1640 medium. In vitro primed immune cells were incubated with 2×10³ 51Cr-labeled target cells in 0.2 ml of complete medium containing 10% FCS in V-bottom plates for 4 hours. A range of effector-to-target cell ratios were used in the experiments. An aliquot of the culture fluid was counted in a gamma scintillation counter. Cytotoxic T cell activity was calculated as described in section 5.5. The spontaneous $^{51}Cr$ release was determined by incubation of targets in complete medium. The maximal $^{51}Cr$ release was determined by incubation of targets in TNEN.

To increase cytotoxic activity, the mixed cell cultures were restimulated on day 9 or 10 by culturing in the presence of feeder cells and rat Con A. The mixed cell cultures were restimulated one or more times, any subsequent restimulations were done with 5 to 10 days in between restimulations. The in vitro primed cells were collected from the wells, spun down at 700 g–2500 g in a standard laboratory centrifuge at 4° C., resuspended in 24 ml of complete RPMI 1640 and plated out (1 ml per well) in the wells containing feeder cells and 10% rat Con A.

In order to prepare the feeder cells, 1×10⁸ spleen cells were irradiated for 10 min (800 rads/min), washed and resuspended in 24 ml of complete RPMI 1640 medium containing 10% rat Con A—stimulated spleen cell supernatant or recombinant human IL-2. One million target cells were irradiated for 30 min (800 rads/min), washed and added to the irradiated spleen cells in rat Con A. The mixture of cells were plated out in 24 wells (1 ml per well).

On day six after restimulation, cytotoxicity of the in vitro primed T cells were determined by the assay as described supra.

6.3 RESULTS

The following experiments were performed to illustrate the methods of the present invention. Spleen cells isolated from C57BL/6 mice were primed in vitro according to the procedure described in section 6.2 using the following mock-loaded cancer cells: SVB6, EG7 and N1. Similarly, spleen cells of C3H-He mice were primed in vitro with mock-loaded PS-C3H cancer cells. Mock-loading as used herein refers to the treatment of antigenic cells with osmotic shock and irradiation and was carried out as described in section 6.2. As controls, spleen cells from C57BL/6 and C3H-He were stimulated by co-culturing with cancer cells that were not treated with osmotic shock.

The antigen-specific cytotoxicity of the responding T cells in the in vitro primed cell cultures were tested by the four-hour $^{51}Cr$ release assay as described in section 6.2. The amount of $^{51}Cr$ release measures the degree of target cell lysis mediated by the cytotoxic T cells in the four-hour period. Antigenic cells that were used in the in vitro priming reaction were used as target cells. Other cancer cells were used as control target cells to demonstrate the specificity of the cytotoxic effect.

Figure 1A:
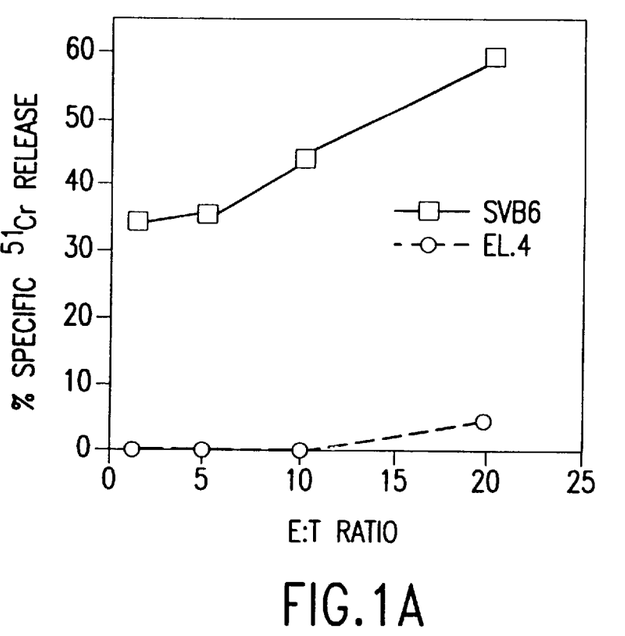
FIGS. 1A–1B. Reactivity of immune cells activated in vitro by SVB6 cancer cells. Naive spleens cells from C57BL/6 mice were stimulated in vitro with mock-loaded SVB6 cells (FIG. 1A) and untreated SVB6 cells (FIG. 1B). The results were determined by a 4-hour cytotoxicity assay, and expressed in percentages of $^{51}Cr$ released from target cells (due to their lysis), at various ratios of activated immune cells (effector cells (E) to target cells (T), i.e., E:T ratio). SVB6 cells (open squares) were used as target cells, and EL4 cells (open circles) were used as negative control target cells.
Figure 1B:
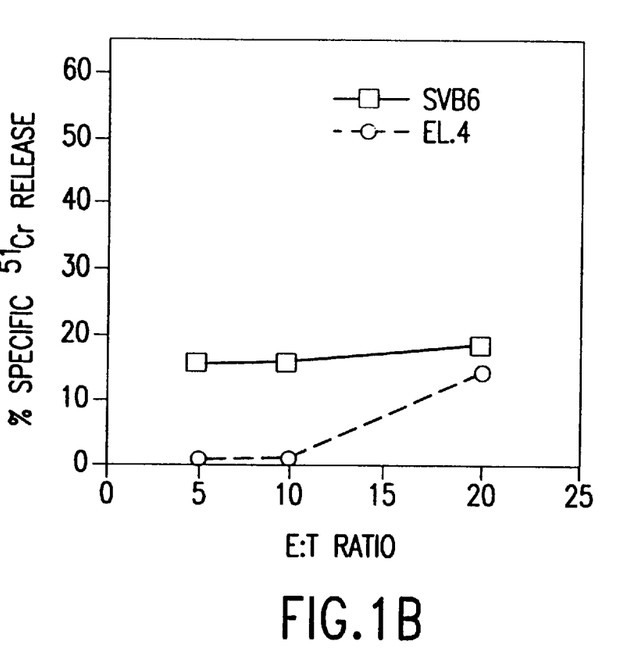
Figure 2A:
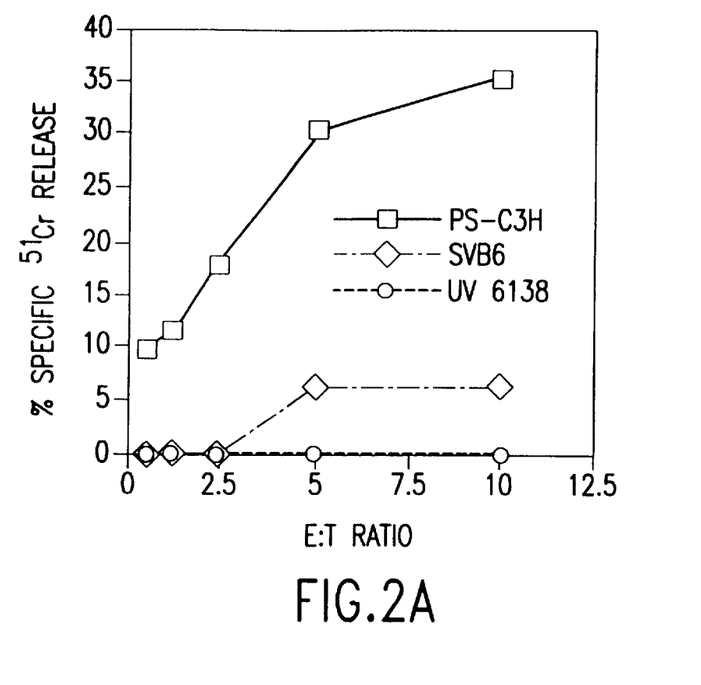
FIGS. 2A–2B. Reactivity of immune cells activated in vitro by PS-C3H cancer cells. Naive spleen cells from C3H-HeJ mice were primed with mock-loaded PS-C3H cells (FIG. 2A) and untreated PS-C3H cells (FIG. 2B). The results were determined and expressed as described above for FIGS. 1A–1B. PS-C3H cells (open squares) were used as target cells, and SVB6 (open diamonds) and UV 6138 (open circles) cancer cells were used as negative control target cells.
Figure 2B:
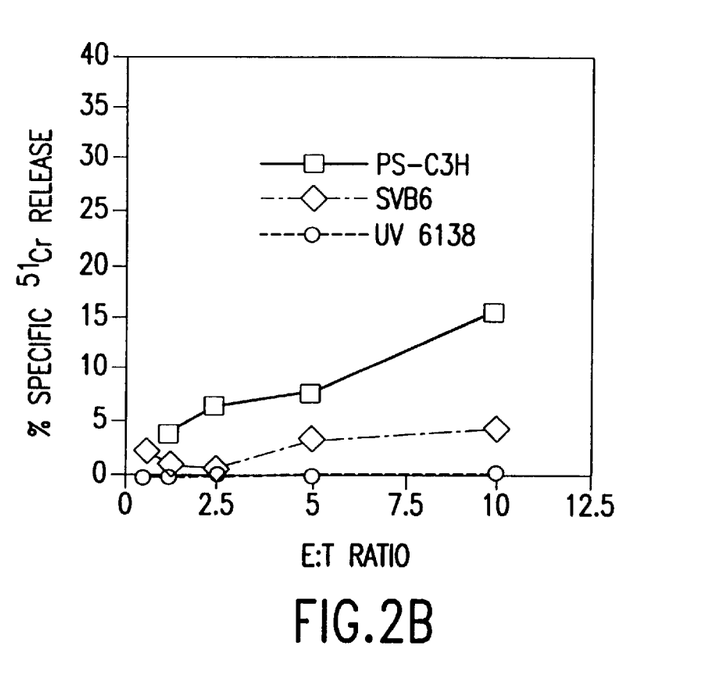
Figure 3A:
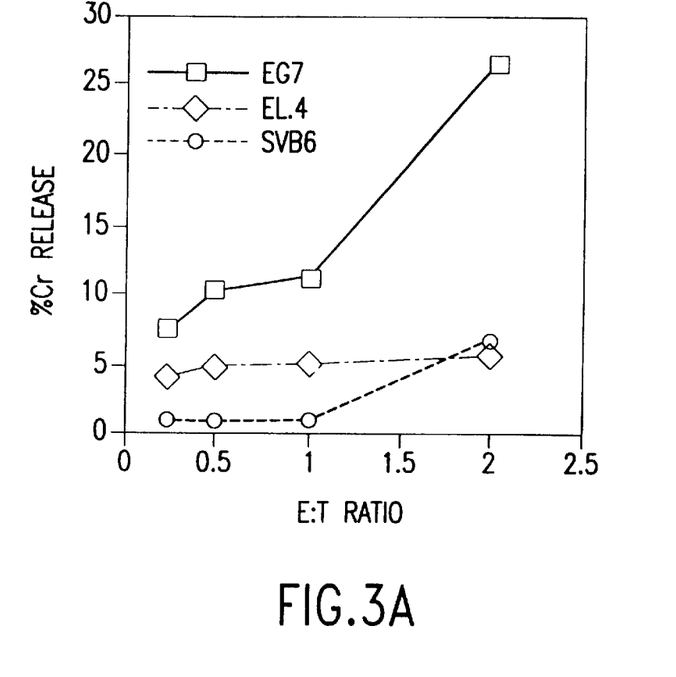
FIGS. 3A–3B. Reactivity of immune cells activated in vitro by EG7 cancer cells. Naive spleen cells from C57BL/6 mice were primed in vitro with mock-loaded EG7 cells (FIG. 3A) and untreated EG7 cells (FIG. 3B). The results were determined and expressed as described above for FIGS. 1A–1B. EG7 cells (open squares) were used as target cells, and SVB6 (open circles) and EL4 (open diamond) cancer cells were used as negative control target cells.
Figure 3B:
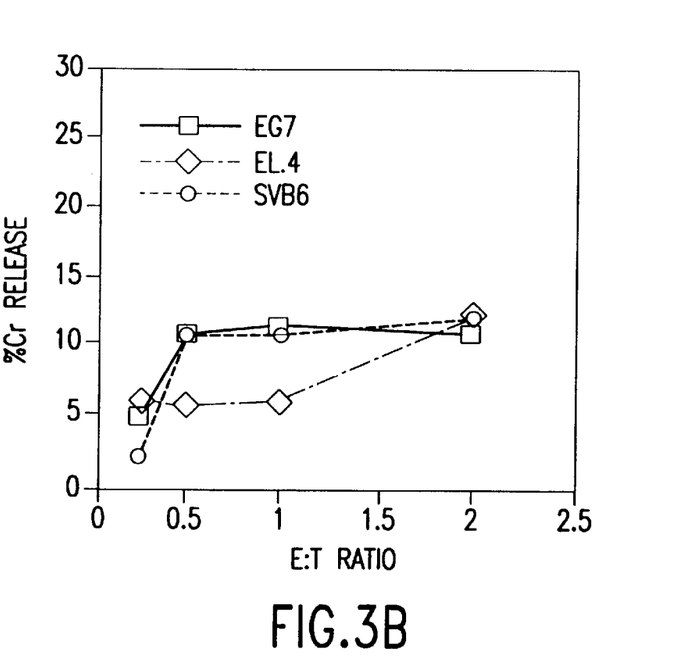
Figure 4A:
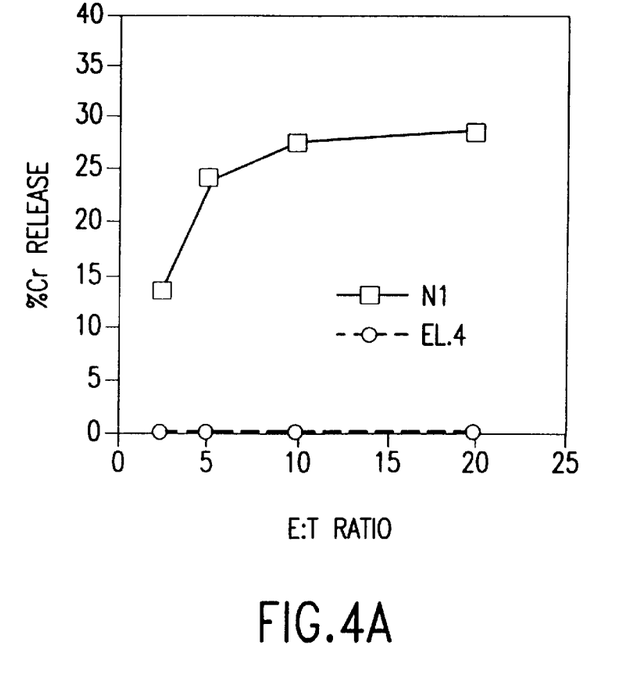
FIGS. 4A–4B. Reactivity of immune cells activated in vitro by N1 cancer cells. Naive spleen cells from C57BL/6 mice were primed in vitro with mock-loaded N1 cells (FIG. 4A) and untreated N1 cells (FIG. 4B). The results were determined and expressed as described above for FIGS. 1A–1B. N1 cells (open squares) were used as target cells, and EL4 (open circles) cancer cells were used as control target cells.
Figure 4B:
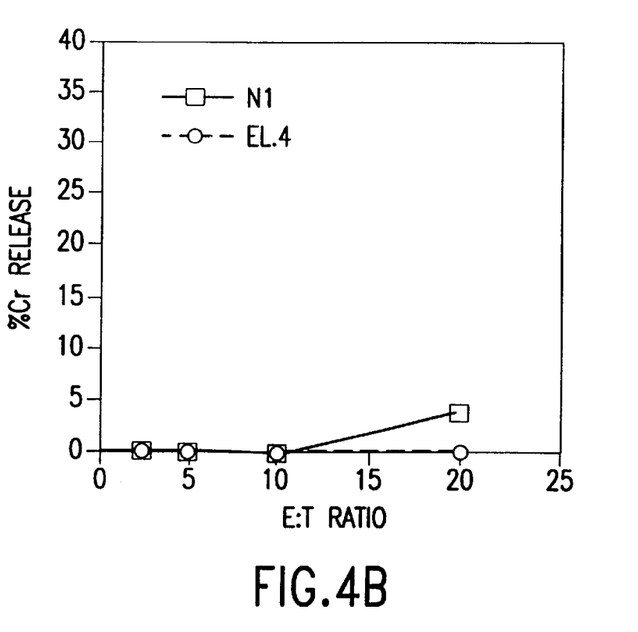

Using C57BL/6 spleen cells and mock-loaded SVB6, EG7 and N1 cells, the amount of $^{51}Cr$ released as a result of target cell lysis mediated by cytotoxic T cells generated by the mock-loaded cancer cells (FIGS. 1A, 3A and 4A) was significantly and consistently higher than that mediated by T cells generated by untreated antigenic cells (FIGS. 1B, 3B and 4B). Similarly, cytotoxic T cells generated from C3H-He spleen cells using mock-loaded PS-C3H cells (FIG. 2A) were more efficient at lysing target cells than the control (FIGS. 2A–2B). Thus, the cytotoxic effect generated by mock-loaded antigenic cells of the present invention is significantly stronger than using untreated cancer cells, especially at higher effector:target cell ratios.

Furthermore, the cytotoxic effect generated by stimulation with mock-loaded cancer cells is antigen specific. Cytotoxic T cells generated by stimulation with mock-loaded SVB6 cells have little or no cytotoxic effect on EL4 cells (FIG. 1A). Likewise, cytotoxic T cells generated using mock-loaded EG7 or N1 cells were significantly less reactive against, respectively, the control EL4 and SVB6 cells (FIG. 3A), and the control EL4 cells (See FIG. 4A).

Cytotoxic T cells stimulated with mock-loaded PS-C3H cells had no cytolytic effect on control UV6138 cells and very limited activity on control SVB6 cells.

In summary, antigenic cells treated according to the methods of the invention can stimulate in vitro the activation of T cells that can mediate an effective antigen-specific cytotoxic T cell response. Thus, administration of such in vitro generated antigen-reactive cytotoxic T cells to a MHC-matched recipient, as described herein, represents a therapeutic or preventative approach for a wide range of cancers or infectious diseases.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for generating cytotoxic T cells specific to antigenic cells displaying an antigenicity of interest comprising the following steps in the order stated:
   (a) subjecting live antigenic cells that are animal cells displaying an antigenicity of interest to osmotic shock in vitro;
   (b) subjecting the antigenic cells to irradiation in vitro;
   (c) culturing the antigenic cells with immune cells comprising T cells and antigen presenting cells in vitro, wherein the antigenic cells and T cells have at least one common MHC allele,
   such that the T cells become activated, thereby generating cytotoxic T cells that are specific to the antigenicity of interest displayed by the antigenic cells.

2. The method of claim 1 in which the subjecting to osmotic shock is carried out by a method comprising the following steps in the order stated:
   (a) incubating the antigenic cells in a hyperosmotic buffer; and
   (b) incubating the antigenic cells in a hypotonic buffer.

3. A method for generating cytotoxic T cells specific to antigenic cells displaying an antigenicity of interest comprising culturing in vitro immune cells comprising T cells and antigen presenting cells with antigenic cells displaying an antigenicity of interest, such that the T cells become activated, thereby generating cytotoxic T cells that are specific to the antigenicity of interest displayed by the antigenic cells, wherein the antigenic cells are animal cells that are the product of a method comprising subjecting in vitro the antigenic cells displaying the antigenicity of interest to osmotic shock followed by irradiation, and wherein the antigenic cells and T cells have at least one common MHC allele.

4. The method of claim 1, 2 or 3 wherein the immune cells and antigenic cells are human cells.

5. The method of claim 1, 2 or 3 wherein the immune cells and antigenic cells are derived from the same human.

6. The method of claim 1 further comprising recovering the cytotoxic T cells from the cell culture.

7. The method of claim 1 wherein the immune cells comprise peripheral blood lymphocytes.

8. The method of claim 1 wherein the immune cells are whole blood leukocytes.

9. The method of claim 1 wherein the antigenic cells are cancer cells.

10. The method of claim 2 wherein the antigenic cells are cancer cells.

11. The method of claim 3 wherein the antigenic cells are cancer cells.

12. The method of claim 9 wherein the cancer cells are of a cancer selected from the group consisting of sarcoma, carcinoma, leukemia, lymphoma and myeloma.

13. The method of claim 9 wherein the cancer cells are of a prostate cancer.

14. The method of claim 9 wherein the cancer cells are of a breast cancer.

15. The method of claim 9 wherein the cancer cells are of a colon cancer.

16. The method of claim 1 wherein the antigenic cells are infected cells.

17. The method of claim 2 wherein the antigenic cells are infected cells.

18. The method of claim 3 wherein the antigenic cells are infected cells.

19. The method of claim 16, 17 or 18 wherein the antigenic cells are infected by a virus, bacterium, fungus, parasite, or protozoan.

20. The method of claim 1, 2 or 3 wherein the antigenic cells recombinantly express an antigen.

21. The method of claim 1 wherein the antigenic cells recombinantly express an antigen of a pathogen.

22. The method of claim 1 wherein the antigenic cells recombinantly express an antigen of a cancer cell.

23. The method of claim 1 wherein the antigenic cells have been induced in vitro to become cancer or transformed cells.

24. The method of claim 1, 2 or 3 wherein the antigenic cells have been infected in vitro by a pathogen.

25. The method of claim 2 wherein the hyperosmotic buffer has an osmotic pressure in the range of about two to five times the physiological osmotic pressure inside a cell, and the hypotonic buffer has an osmotic pressure in the range of about 0.2 to 0.9 times the physiological osmotic pressure inside a cell.

26. The method of claim 2 wherein the hyperosmotic buffer has an osmotic pressure of about three times the physiological osmotic pressure inside a cell, and the hypotonic buffer has an osmotic pressure of about two-thirds times the physiological osmotic pressure inside a cell.

27. The method of claim 9, 10 or 11 wherein the immune cells and antigenic cells are derived from the same human.

28. The method of claim 16 wherein the immune cells and antigenic cells are derived from the same human.

29. The method of claim 19 wherein the immune cells and antigenic cells are derived from the same human.

30. The method of claim 1 further comprising restimulating the immune cells at least one with said antigenic cells that have been irradiated.

31. A method for generating cytotoxic T cells specific to antigenic cells displaying an antigenicity of interest comprising the following steps in the order stated:
   (a) incubating live antigenic cells that are animal cells displaying an antigenicity of interest in a hyperosmotic buffer for 5 to 60 minutes at 37° C.;
   (b) incubating the antigenic cells in a hypertonic buffer for 1 to 10 minutes at 37° C.;
   (c) irradiating the antigenic cells with 1,000 to 10,000 rads; and
   (d) culturing the antigenic cells in vitro with immune cells comprising T cells and antigen presenting cells at a ratio of about 1:100 antigenic cells:immune cells for 3 to 9 days at 37° C.,
   such that the T cells become activated, thereby generating cytotoxic T cells that are specific to the antigenicity of interest displayed by the antigenic cells.

32. A method for generating cytotoxic T cells specific to antigenic cells displaying an antigenicity of interest comprising the following steps in the order stated;

(a) incubating two million to three million live antigenic cells that are animal cells displaying an antigenicity of interest in 0.5 ml of a first buffer consisting of 0.5 M sucrose, 10% polyethylene glycol, 10 mM HEPES buffer and RPMI 1640 for 10 minutes at 37° C.;

(b) adding to the antigenic cells in the first buffer, 15 ml of a second buffer consisting of a 3:2 ratio of RPMI 1640:water, and incubating the antigenic cells in the resulting buffer for 3 minutes at 37° C.;

(c) incubating the antigenic cells in culture medium for two hours at 37° C.;

(d) irradiating the antigenic cells at 300 rads/minutes for 30 minutes in 3 ml of culture medium; and (e) culturing the antigenic cells with spleen cells or whole blood leukocytes at a ratio of 1:100 antigenic cells to spleen cells or whole blood leukocytes, in culture medium at 37° C. for about 6 days, such that T cells among said spleen cells or whole blood leukocytes become activated, thereby generating cytotoxic T cells that are specific to the antigenicity of interest displayed by the antigenic cells.

33. The method of claim 1, 2 or 3 wherein the antigenic cells and the immune cells are purified.

34. The method of claim 31 or 32 wherein the antigenic cells are cancer cells.

* * * * *